United States Patent
Gupta et al.

(10) Patent No.: US 9,078,972 B2
(45) Date of Patent: Jul. 14, 2015

(54) HIGH FLUX BASKET CATHETER FOR EFFICIENT, CONTINUOUS FLOW PERITONEAL DIALYSIS

(71) Applicants: Anmol Gupta, Fort Lauderdale, FL (US); Bharat K. Gupta, Fort Lauderdale, FL (US); Mohit Gupta, Fort Lauderdale, FL (US)

(72) Inventors: Anmol Gupta, Fort Lauderdale, FL (US); Bharat K. Gupta, Fort Lauderdale, FL (US); Mohit Gupta, Fort Lauderdale, FL (US)

(*) Notice: Subject to any disclaimer, the term of this patent is extended or adjusted under 35 U.S.C. 154(b) by 29 days.

(21) Appl. No.: 13/961,918

(22) Filed: Aug. 8, 2013

(65) Prior Publication Data

US 2014/0058316 A1    Feb. 27, 2014

Related U.S. Application Data

(63) Continuation-in-part of application No. 13/592,712, filed on Aug. 23, 2012.

(51) Int. Cl.
| | | |
|---|---|---|
| *A61M 3/00* | (2006.01) | |
| *A61M 1/28* | (2006.01) | |
| *A61M 25/00* | (2006.01) | |

(52) U.S. Cl.
CPC .............. *A61M 1/285* (2013.01); *A61M 1/284* (2014.02); *A61M 25/0071* (2013.01); *A61M 25/0074* (2013.01); *A61M 2025/0031* (2013.01); *A61M 2025/0073* (2013.01)

(58) Field of Classification Search
CPC .............. A61M 1/284–1/285; A61M 25/0071; A61M 25/0074; A61M 2025/0031; A61M 2025/0073
USPC ................................................ 604/29, 43, 27
See application file for complete search history.

(56) References Cited

U.S. PATENT DOCUMENTS

| | | | |
|---|---|---|---|
| 4,437,856 A * | 3/1984 | Valli | .............................. 604/29 |
| 5,254,084 A | 10/1993 | Geary | |
| 5,807,311 A | 9/1998 | Palestrant | |

(Continued)

FOREIGN PATENT DOCUMENTS

| | | |
|---|---|---|
| AU | 2003212961 A1 | 9/2003 |
| AU | 2003272564 A1 | 5/2004 |

(Continued)

OTHER PUBLICATIONS

International Preliminary Report on Patentability dated Feb. 24, 2015 and Written Opinion dated Nov. 8, 2013 for PCT/US2013/054266, 9 pages.

*Primary Examiner* — Edelmira Bosques
(74) *Attorney, Agent, or Firm* — Ryan S. Osterweil; Day Pitney LLP

(57) ABSTRACT

A catheter for use in continuous flow peritoneal dialysis comprising an inflow tube and outflow tube, both connected on one end to a dialysis machine. The inflow tube is divided into a plurality of inflow auxiliary tubes, and the outflow tube is divided into a plurality of outflow auxiliary tubes, with all auxiliary tubes encased in a single external tube. The auxiliary tubes each contain a plurality of apertures for the rapid and efficient movement of dialysis solution in and out of the peritoneal cavity to reach a larger surface area without kinking or blocking. The external tube comprises a tunnel for insertion of a fiber optic borescope to view the dialysis procedure. The auxiliary tubes are covered by a sheath prior to implantation, which is then removed, deploying, preferably into an open-basket shape, the auxiliary tubes within the peritoneal cavity to allow for the continuous flow of dialysis solution.

14 Claims, 8 Drawing Sheets

(56) References Cited

U.S. PATENT DOCUMENTS

| | | |
|---|---|---|
| 6,758,836 B2 | 7/2004 | Zawacki |
| 6,814,718 B2 | 11/2004 | McGuckin, Jr. et al. |
| 6,858,019 B2 | 2/2005 | McGuckin, Jr. et al. |
| 6,913,590 B2 | 7/2005 | Sorenson et al. |
| 6,986,752 B2 | 1/2006 | McGuckin, Jr. et al. |
| 7,011,645 B2 | 3/2006 | McGuckin, Jr. et al. |
| 7,074,213 B2 | 7/2006 | McGuckin, Jr. et al. |
| 7,077,829 B2 | 7/2006 | McGuckin, Jr. et al. |
| 7,097,635 B2 | 8/2006 | McGuckin, Jr. et al. |
| 7,204,831 B2 | 4/2007 | McGuckin, Jr. et al. |
| 7,390,322 B2 | 6/2008 | McGuckin, Jr. et al. |
| 7,566,316 B2 | 7/2009 | McGuckin, Jr. et al. |
| 7,799,014 B2 | 9/2010 | McGuckin, Jr. et al. |
| 8,021,321 B2 | 9/2011 | Zawacki |
| 8,323,228 B2 | 12/2012 | DeFonzo et al. |
| 8,500,674 B2 | 8/2013 | DeFonzo et al. |
| 2002/0091352 A1 | 7/2002 | McGuckin, Jr. et al. |
| 2002/0107506 A1 | 8/2002 | McGuckin, Jr. et al. |
| 2002/0120227 A1* | 8/2002 | Childers et al. ............. 604/29 |
| 2002/0121282 A1 | 9/2002 | McGuckin, Jr. et al. |
| 2002/0123715 A1 | 9/2002 | Sorenson et al. |
| 2003/0093027 A1 | 5/2003 | McGuckin, Jr. et al. |
| 2003/0093029 A1 | 5/2003 | McGuckin, Jr. et al. |
| 2003/0093090 A1 | 5/2003 | McGuckin, Jr. et al. |
| 2004/0210187 A1 | 10/2004 | Zawacki |
| 2005/0054989 A1 | 3/2005 | McGuckin, Jr. et al. |
| 2005/0090776 A1 | 4/2005 | McGuckin, Jr. et al. |
| 2005/0131340 A1 | 6/2005 | Sorenson et al. |
| 2005/0131341 A1 | 6/2005 | McGuckin, Jr. et al. |
| 2006/0259007 A1 | 11/2006 | McGuckin, Jr. et al. |
| 2006/0270962 A1 | 11/2006 | McGuckin, Jr. et al. |
| 2008/0097382 A1 | 4/2008 | McGuckin, Jr. et al. |
| 2008/0312578 A1 | 12/2008 | DeFonzo et al. |
| 2009/0312687 A1 | 12/2009 | DeFonzo et al. |
| 2011/0015559 A1 | 1/2011 | McGuckin, Jr. et al. |

FOREIGN PATENT DOCUMENTS

| | | |
|---|---|---|
| AU | 2002249904 B2 | 2/2006 |
| CA | 2272336 A1 | 6/1998 |
| CA | 2432330 A1 | 8/2002 |
| CA | 2474351 A1 | 8/2003 |
| CA | 2501545 A1 | 5/2004 |
| CA | 2751702 A1 | 5/2004 |
| CA | 2629007 A1 | 10/2008 |
| EP | 0961628 A1 | 7/2004 |
| EP | 1471966 A1 | 11/2004 |
| EP | 0961628 B1 | 12/2004 |
| EP | 1556112 A1 | 7/2005 |
| EP | 1383566 B1 | 3/2008 |
| EP | 1556112 B1 | 4/2009 |
| JP | 2005502387 A | 1/2005 |
| JP | 2005516693 A | 6/2005 |
| WO | 9823319 A1 | 6/1998 |
| WO | 02064202 A2 | 8/2002 |
| WO | 03066148 A1 | 8/2003 |
| WO | 2004037331 A1 | 5/2004 |
| WO | PCT/US2013/054266 | 11/2013 |

* cited by examiner

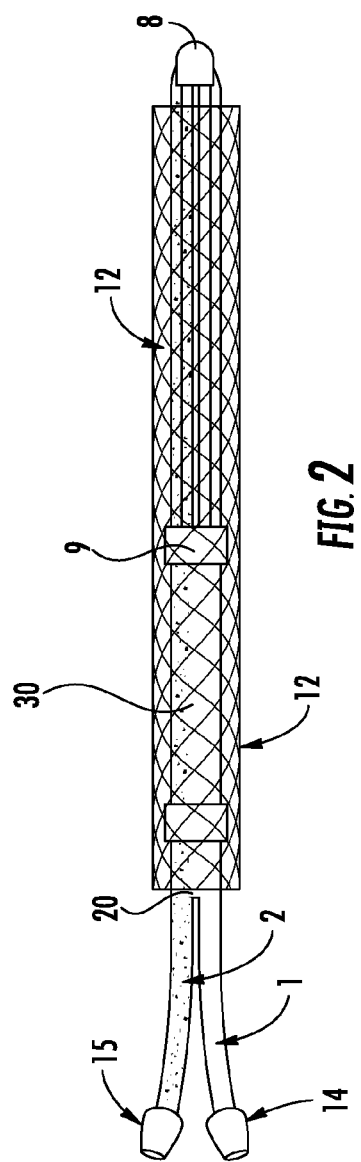
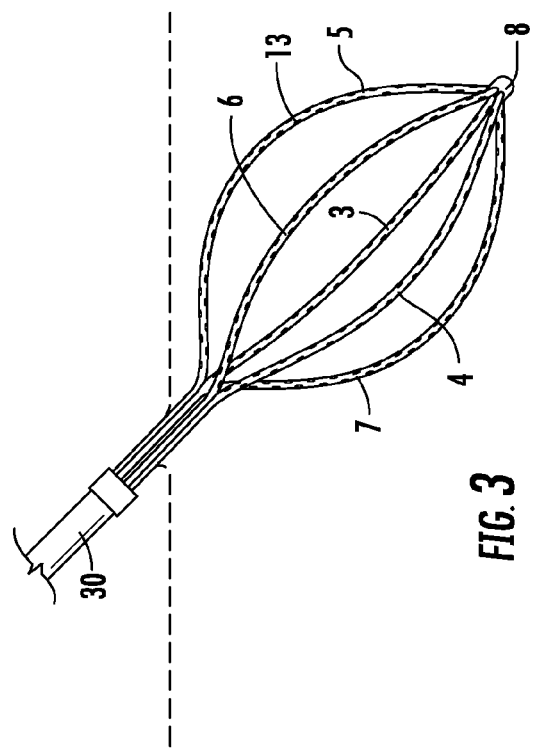

HIGH FLUX BASKET CATHETER FOR EFFICIENT, CONTINUOUS FLOW PERITONEAL DIALYSIS

RELATED APPLICATIONS

This Application is a Continuation-in-Part Application of, and claims priority to, U.S. Non-Provisional application Ser. No. 13/592,712, filed Aug. 23, 2012, the disclosure of which is incorporated herein by reference.

FIELD OF THE INVENTION

The present invention relates to a novel, basket-type silicone dialysis catheter used for providing high-flow, efficient peritoneal dialysis for patients with end-stage renal disease. Disclosed is a new device to be used in continuous flow peritoneal dialysis, which maximizes the efficiency of the dialysis procedure while minimizing the time required for such by utilizing a plurality of inflow and outflow tubes during the dialysis procedure. A new peritoneal dialysis catheter device is presented. In use, the device will provide high-flux simultaneous inflow and outflow of dialysate during peritoneal dialysis. The present invention is preferably made of silicone rubber and Dacron cuffs to anchor the catheter into the abdominal wall. Before implantation, the catheter is preferably encased in a retractable sheath and appears as a straight, single tube for easy implantation in the peritoneal cavity. The sheath is then removed after implantation, and the basket of tubes releases.

BACKGROUND OF THE INVENTION AND DISCLOSURE

Dialysis is a process for removing waste and excess water from the blood, and is used primarily to provide an artificial replacement for lost kidney function in people with renal failure. Dialysis acts as a substitute for the function which the kidneys normally perform in the body, namely regulating the body's fluid balance and removing waste products which accumulate in the body. A patient generally requires dialysis when his body builds up a level of a waste to such a degree that it causes physical illness.

There are two main types of dialysis: hemodialysis and peritoneal dialysis. Hemodialysis uses a special type of filter to remove excess waste products and water from the body. A double lumen catheter is inserted into the patient's chest or neck into a vein. During hemodialysis, the blood is allowed to slowly flow into the catheter and through the filter, called a dialysis membrane, thereby removing any unwanted products or fluids. A solution within the dialysis machine will capture the removed waste products. Once filtered, the clean blood is returned to the body.

Peritoneal dialysis, on the other hand, uses the patient's own body tissues (the peritoneal membrane) inside of the abdominal cavity to act as the filter, rather than using a machine-like filter. Peritoneal dialysis uses a soft tube called a peritoneal catheter to fill the abdomen with a cleansing dialysis solution liquid, called dialysate. The walls of the abdominal cavity and internal viscera are lined with a membrane, called the peritoneum, which acts as dialysis membrane. The peritoneal membrane separates two fluid-containing compartments—(a) the blood in the peritoneal capillaries, which in kidney failure patients accumulates waste products such as urea, creatinine, potassium etc.; and (b) the dialysis solution. The peritoneal membrane allows waste products and extra fluid to pass from the blood into the dialysis solution by process of diffusion and ultrafiltration occurring simultaneously. The dialysis solution is then drained from the abdomen, and takes with it the waste products (the solute) which were previously cleared therein. The process of introducing the dialysis solution into the body and removing the excess of fluids (water) and solute is called an exchange, and the period of time in which the dialysis solution is in the abdomen is called the dwell.

Peritoneal dialysis affords patients greater independence and flexibility in their dialysis schedules and location, while its simplicity, safety profile and cost-effectiveness, when compared to home hemodialysis, make it an ideal dialysis modality, especially for younger, working patients. Major obstacles of peritoneal dialysis include catheter-related complications, loss of efficiency of the peritoneal membrane over time, and long hours of dialysis; this invention seeks to address and minimize these obstacles.

Over the last several years, automated peritoneal dialysis (APD) has emerged as the preferred modality of peritoneal dialysis amongst patients and healthcare providers. In automated peritoneal dialysis, the above-mentioned process occurs using a small and lightweight cycler machine while an individual is sleeping. In the United States, two types of automated peritoneal dialysis devices or methods are employed—continuous cycling peritoneal dialysis (CCPD) or nocturnal intermittent peritoneal dialysis (NIPD). CCPD uses an automated cycler to perform multiple exchanges of fluid during the night while the patient sleeps, and then leaves the dialysis solution in the abdomen for the patient to have one more exchange take place which lasts the entire day. NIPD, alternatively, makes more exchanges during the night, and does not require the final exchange during the day.

Another technique is known as Tidal Peritoneal Dialysis (TPD), which provides a high-dialysate flow rate and consequently an increased diffusion gradient between the blood and the dialysate. This minimizes the formation of unstirred layers of dialysate. Continuous contact between the dialysate and peritoneal membrane also provides continuous removal of solute and water, not just intermittent removal during the dwell period. Finally, in some European countries, Continuous Flow Peritoneal dialysis (CFPD) is also used, especially for patients with limited efficiency in standard CAPD (continuous ambulatory peritoneal dialysis) or APD (automated peritoneal dialysis). CFPD provides a continuous movement of dialysate into and out of the abdomen.

Regardless of the technique employed for peritoneal dialysis, all current peritoneal access devices or peritoneal catheters have several typical disadvantages or complications. These common complications include peri-catheter leaks and outflow failure caused by a diminished volume of fluid in the peritoneal cavity. These occur frequently, particularly in the latter stages of the fluid drain, when resistance to fluid outflow increases, and when the bowel loops move closer to the standard catheter tip and side holes, thus causing blockages and preventing the free movement of dialysate in and out of the catheter.

Another limitation in current peritoneal dialysis devices is an inefficient use of the peritoneal membrane surface area. Peritoneal membranes have a surface area of approximately 1,200 square centimeters per square meter of body surface area, or 2,200 square centimeters in an average adult. In current clinical applications of peritoneal dialysis, however, only limited parts of the surface area are seemingly utilized during the procedure. The surface area which is actually contacted during dialysis depends on the position of the catheter and patient. The position of the catheter, if bunched up or blocked in any way such as in an adhesion formation, can cause dialysate fluid to be trapped in pockets that do not participate in the fluid exchange. These issues result in a lengthier period of time required for the removal of all waste from the system, and increases costs as greater amounts of dialysate are required to complete the procedure. This could also result in excess dialysate being trapped in the abdomen.

Another major problem with current peritoneal dialysis is infection. Because of the nature of the machinery used for the procedure, a plastic tube runs from inside the peritoneal cavity to the outside of the body. This creates the potential for bacteria to enter the body, especially if the tubes are not cleaned or used properly.

An additional limitation to current dialysis methods is time. Hemodialysis requires minimal participation by the patient during treatment but requires the patients adhere to very specific schedules and diets. Peritoneal dialysis allows for more flexible scheduling, but requires many hours of dialysis each day and must be done every day of the week. The process of filling the abdomen with dialysis solution, allowing it to mix with the unwanted waste in the body, and then draining the mixture, takes a lengthy period of time. A typical dialysis schedule requires multiple cycles daily, each taking approximately 4 to 6 hours.

The present invention discloses a new and novel peritoneal dialysis catheter. The present invention preferably comprises the use of a silicone catheter device, which is preferably 320 mm long. The tube preferably has an inner diameter of 3.5 mm and an outer diameter of 4.0 mm, although the use of alternate dimensions for the catheter is envisioned as well. The large tube is sub-divided into a plurality of smaller tubes, and preferably six. The plurality of smaller tubes comprises one or more (preferably two) inflow paths, one or more (preferably three) outflow paths, and at least one tube to permit insertion of a fiber optic borescope to permit seeing inside the peritoneal cavity during dialysis.

In the preferred embodiment, a total of six small tubes are present within the large tube comprising the silicone catheter. Preferably, this includes three outflow tubes, two inflow tubes, and one tube for insertion of the fiber optic borescope. In an alternate embodiment, a separate tube for receipt of the fiber optic scope is not needed, and one inflow tube may be used for receipt of the same. Preferably, the plurality of tubes only extends through part of the main catheter tube, preferably 150 mm. This is at the end of the tube which is inserted into the peritoneal cavity. The plurality of tubes are thus encased in a single external silicone large tube for easy insertion into the peritoneal cavity. At the proximal end, i.e., the end of the tube which connects to a dialysis machine, there is preferably provided a large-diameter bore, single inflow tube and a single outflow tube. The single inflow tube can be connected to a dialysis machine with dialysis fluid to be pumped into the peritoneal cavity, while the single outflow tube can be connected to a drainage bag for all fluid removed from the body during the dialysis process.

In the main section, preferably about 150 mm in length, the large single outflow tube and the large single inflow tube preferably split into the plurality of smaller inflow and outflow tubes. All of the inflow and outflow tubes are encased in an external silicone large tube. Preferably, the single outflow tube trifurcates into three smaller outflow tubes and the single inflow tube preferably bifurcates into two smaller inflow tubes. The split from single inflow and outflow tubes into the plurality of tubes occurs preferably at the location that the large inflow tube and large outflow tube connect in the single encasing and external tube. The outflow tubes preferably merge into outlet tail end and the inflow tubes preferably merge into an inflow tail end, preferably in a Y-shape formation.

The base of the Y-shaped formation, where the inflow tube and outflow tube connects, preferably also provides a tube for selective insertion of a fiber optic borescope, to allow a physician performing the dialysis using the present invention to see inside the peritoneal cavity to ensure that the dialysis is performing properly. In an alternate embodiment, a separate tube for receipt of the fiber optic scope is not needed, and one inflow tube may be used for receipt of the same. The tube for allowing insertion of the fiber optic borescope preferably only extends the length of the large encasing tube where the inflow and outflow tubes branch into a plurality of smaller tubes within the peritoneal cavity. In the preferred embodiment, the tunnel for insertion of the fiber optic borescope opens at the junction of the Y where the inflow tubes and outflow tubes meet. The Y-shaped tail, where the tubes all connect, constitutes the initial or extra-abdominal portion of the silicone catheter. The preferably terminal or intra-abdominal smaller tubes, preferably comprising two inflow tubes, three outflow tubes, and a borescope tube, are preferably encased in an expandable sheath. The sheath is used to hold the plurality of tubes in place during implantation of all tubes into the peritoneal cavity.

After intra-peritoneal implantation of the catheter, the outer sheath surrounding the tubes is pulled out. This will have the effect of separating and deploying the plurality of tubes. All tubes take the shape of a basket or tubes forming the outside of an elongated football or some other rounded structure. Each of the tubes contains numerous side perforations of preferably 0.5 mm or smaller. For the ease of implantation, the tubes are preferably joined together at an end cap, which allows the easiest access of the tubes into the abdomen or peritoneal cavity of a patient, and requires the smallest possible aperture through which to do so.

The middle portion of the silicone catheter appended to two Dacron cuffs that are preferably 70 mm apart. A Dacron cuff is a sheath of synthetic fabric which surrounds the inflow and outflow tubes of the catheter to prevent accidental displacement of the tubes. One Dacron cuff is preferably placed on the tubing at the skin level, while the other is preferably placed around the tubing at the peritoneal level. The Dacron felt cuffs are used to create a biological barrier against bacterial invasion at the interface between implanted foreign synthetic materials, i.e. silicone tubes and the skin. After implantation of peritoneal catheter, body tissues grow into the Dacron felt cuff, thus stabilizing the catheter and forming a biological barrier against infection. The second cuff is located just outside the peritoneal cavity, thus closing the sinus tract at that level. The growth of fibroblasts and tissues into the meshwork of Dacron cuffs not only fixes the catheter in place and prevents sliding, but also provides an efficient barrier against bacterial invasion. By 10-14 days, tissue ingrowth into the cuffs is virtually complete throughout its thickness.

The initial, or extra-abdominal, portion of the catheter that runs outside of the skin simply provides a means for connecting the inflow and outflow tubes to the peritoneal dialysis apparatus. This portion of the tubing preferably contains a single inflow tube and a single outflow tube for movement of the dialysis solution in and out of the peritoneal membrane. Therefore, in the preferred embodiment of the present invention, all dialysate which enters the inflow tube from the dialysis machine will travel through a single inflow tube until entering the peritoneal cavity, at which point it will disperse into the plurality of inflow tubes to maximize the surface area of the membrane. Then, preferably, the dialysate fluid, along with waste products and excess body water (ultrafiltration), is collected to exit the peritoneal membrane. It will enter into a plurality of the outflow tubes, which will all converge into a single outflow tube upon exit from the abdomen, such that the fluid will travel back to the drainage bag.

Implantation of the present invention is made using open surgical technique or standard laparoscopic methodology, depending on the surgeon's interest and expertise. The laparoscopic technic is becoming more popular because of its advantages in direct visualization of the catheter placement and also in the ability to perform a partial omentectomy or lysis of adhesions during the catheter placement. In the laparoscopic technique, a patient is operated on under general anesthesia. A small incision is made in the abdomen for placement of the catheter, and a tunnel is created into the patient's peritoneal cavity. The invention, multiple tubes or tubes held together by a sheath, is then inserted through the tunnel and into the cavity. After implantation, the surrounding sheath will be retracted from the tubing, thereby leaving behind a basket-shaped system of auxiliary inflow and outflow tubes in the intra-peritoneal cavity. The catheter is placed under direct vision to ensure proper positioning. An internal Dacron cuff is placed at pre-peritoneal space. Using reabsorbable sutures, which prevent obstruction of the catheter dialysate leakage, the surgeon closes the peritoneum and rectus sheaths. Subsequently a tunnel is created under the abdominal wall skin, and a distal or external Dacron cuff is placed under the skin at the catheter exit site. The catheter is tested before closing the incision.

This is the crux of the present invention as it differs from all prior dialysis catheters, which comprise merely a single tube for both inflow and outflow of dialysate. Compared to a single tube or single coiled tube peritoneal dialysis catheter (which is the standard catheter used in the field presently), the present inventive catheter device will occupy a larger surface area of the peritoneal cavity and allow for smaller pockets of the peritoneal cavity to participate in peritoneal dialysate exchange with blood capillaries. This not only acts to improve the efficiency of the peritoneum as a dialysis membrane, but it also reduces future pocket formations within the peritoneal membrane by adhesions and other bodily organs such bowel loops. Such pocket formations often occur after a patient suffers from episodes of peritonitis, or inflammation or irritation of the peritoneum.

Due to the basket-shape of the present invention after implantation, the chances of catheter kinking, or curling in on itself, or omentum wrapping are negligible compared to a single tube straight or coiled catheter. In traditional peritoneal dialysis, a single catheter is used which frequent has the complication of dialysate out flow failure, where dialysate may be infused into the peritoneal cavity, but fails to drain the fluid out. The outflow failure usually occurs when omentum or bowel loops move closer to traditional catheter and block the catheter tip and side perforations, thereby blocking free drainage of dialysate through these perforations. Outflow failure can also be caused by other means, including the attachment of omentum or other tissues to a single tube or curled catheter tip and side perforations, the migration of single tube traditional catheters (which increases the chance of attachment to omentum), and diminished volume of the fluid in peritoneal cavity during exchange (which inhibits the free flow of dialysate in and out of the catheter and allows for a blockage of inflow or outflow tubes). The present invention overcomes this problem of catheter migration or omentum attachment, as the basket-shaped catheter uses its own three-dimensional structure to push bowel loops and omentum out of the way of the perforations in the tubes for the inflow and outflow of dialysate.

Another advantage of the present invention is the continuous, simultaneous inflow and outflow of fluid. Due to such movement of dialysate, a pressure gradient will be created between the peritoneal fluid volume and the outflow tubes, allowing for free drainage of the fluid and for minimization of the risk of outflow failure. The plurality of inflow and outflow tubes allow the dialysate to enter the peritoneal cavity, and the waste or unwanted fluid mix to exit the peritoneal cavity, at a much more rapid pace than in a traditional peritoneal dialysis system, using a single tube. This provides the advantage of drastically reducing the dwell time needed, since the exchange of the fluids is occurring much quicker and covering a much greater surface area of the membrane. The purpose of the lengthy period of the dwell in traditional peritoneal dialysis is to allow the entire peritoneal membrane to come in contact with the dialysate, thus removing the unwanted waste (solute) and fluids by diffusion and ultrafiltration. In the present invention, substantially the maximum peritoneal surface area and peritoneal capillaries participate in peritoneal transport and therefore the exchange is performed efficiently at a much quicker pace.

Additionally, a multitude of points within the cavity are directly targeted by individual inflow tubes, so there is a limited wait for the dialysate to cover the entire surface area of the membrane. Likewise, a multitude of outflow tubes exist to remove the unwanted solute, ultrafiltered water, and used dialysate from the abdomen upon completion of the dwell. Both of these advantages substantially reduce the time requirement for the dialysis procedure, while also minimizing the recirculation of the same fluid which has already undergone the exchange, thereby improving dialysis clearance. Low dialysis clearance is a frequent problem in single tube or coiled catheter lodged in a peritoneal pocket. Using the present invention, the dialysis procedure can be done efficiently and at a much quicker pace, thereby allowing an individual requiring dialysis multiple times a day greater flexibility in his schedule, while simultaneously obtaining a superior result.

DESCRIPTION OF PRIOR ART

To the Applicants' and Inventors' knowledge, the present invention is a significantly improved design for continuous flow peritoneal dialysis exists which will reduce the potential for outflow failure and maximize participation of the peritoneal membrane while simultaneously reducing the time requirement for the dialysis procedure. No prior art exists which can overcome the manly obstacles and drawbacks facing peritoneal dialysis. Thus, a need presently exists for an improved peritoneal dialysis catheter that: 1) is easier to implant, 2) improves the dialysate inflow distribution; 3) is more efficient in providing a peritoneal exchange mechanism that utilizes the maximum surface area of peritoneal membrane available as a dialyzer; 4) is effective in allowing for a reduced rate of intra-peritoneal dialysate recirculation; 5) reduces trauma to peritoneal membrane; 6) may be used for CAPD, APD, TPD or CFPD techniques of peritoneal dialysis; and 7) provides minimal or no outflow failure. The present inventive catheter will allow for peritoneal dialysis to be a successful modality for long-term dialysis, thereby overcoming many of the aforementioned limitations in current dialysis machines.

SUMMARY OF THE INVENTION

The present invention discloses a catheter, preferably made of silicone, for use in peritoneal dialysis. The basic and main section of the catheter comprises an inner diameter and an outer diameter. The catheter comprises one or more inflow sets of tubes and one or more outflow sets of tubes. The initial or extra-peritoneal portion of the silicone catheter has the inflow tail end and the outflow tail end. Both main tails, i.e., main tail end of outflow tube and main tail end of inflow tube, are connected to a dialysis machine. The opposite end of the catheter device is implanted into the abdominal wall for conducting peritoneal dialysis. On the distal end, the inflow tube preferably bifurcates into two smaller inflow (with respect to the patient) auxiliary tubes, and the outflow tube preferably splits into three smaller outflow auxiliary tubes. All of the smaller auxiliary tubes (preferably five in total) contain a plurality of small side-wall apertures for the rapid and efficient movement of dialysis solution in and out of the peritoneal cavity by passing the same into and out of the tubes. The silicone catheter is preferably provided with two encircling Dacron cuffs to anchor the catheter in abdominal wall tissues after implantation. The distal or intra-abdominal portion of the catheter with tubes is initially covered by a sheath prior to implantation in the peritoneal cavity, for ease of implantation. After the tubes are properly located within the peritoneal cavity, the sheath is removed, thereby deploying and separating the smaller inflow tubes and the smaller outflow tubes within the peritoneal cavity. When released from the sheath, the tubes preferably form an open "basket." Through this device, dialysis solution can continually enter the peritoneal cavity through the apertures in the inflow auxiliary tubes and continually be removed from the peritoneal cavity through the apertures in the outflow auxiliary tubes. This reduces the time required to complete the dialysis exchange procedure and increases its efficiency by (a) maximizing effective surface area of the peritoneal membrane; (b) maximizing the concentration gradient across the peritoneal membrane for solute and water removal; (c) maximizing peritoneal fluid removal by recruiting separate outflow tubes and preventing outflow failure; (d) minimizing the recirculation of dialysate by providing separate inflow and out flow system; and (e) minimizing the time spent on dialysis by continuous and efficient use of dwell time. The present invention also comprises a tube adapted for selective receipt of a fiber optic borescope to allow a physician conducting the dialysis to look into the peritoneal cavity via a real image transfer video camera. The addition of this tube to allow insertion of a fiber optic borescope helps a physician to check on proper functioning of the dialysis and to aid in the diagnosis of any problems presented during the procedure.

BRIEF DESCRIPTION OF THE DRAWINGS

FIG. 2 depicts the present invention in its closed version, i.e. prior to implantation and with the covering sheath thereon;

FIG. 3 depicts the terminal end of the present invention after placement into the peritoneal cavity;

DETAILED DESCRIPTION OF THE DRAWINGS AND THE PREFERRED EMBODIMENT

Description will now be given of the invention with reference to the attached FIGS. 1-7B. It should be understood that these figures are exemplary in nature and in no way serve to limit the scope of the invention as the invention will be defined by the claims, as interpreted by the Courts in an issued U.S. Patent.

Figure 1A:
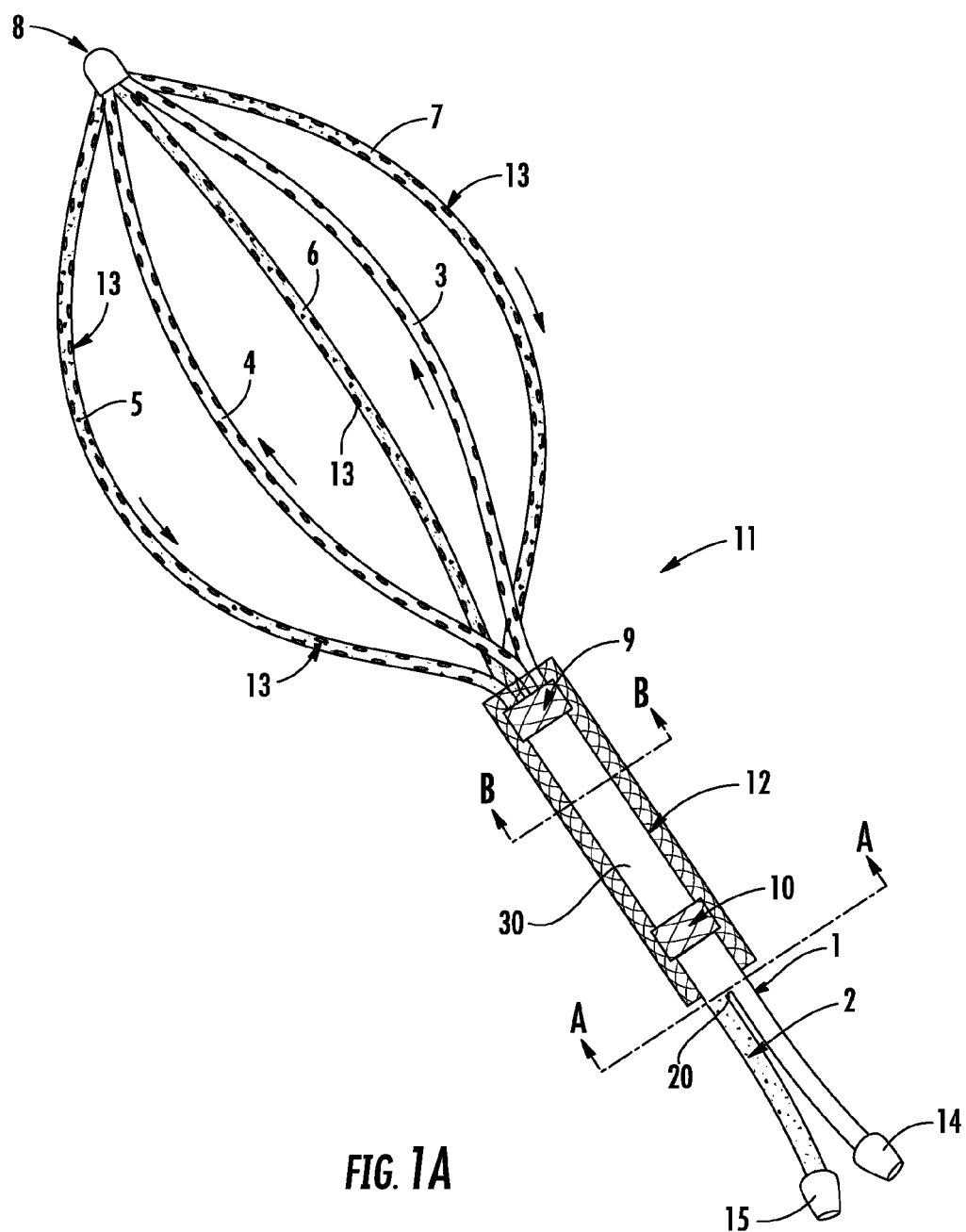
FIG. 1A is a front perspective view the present invention, a high flux basket-like catheter for efficient continuous flow peritoneal dialysis, in its expanded state as would be within the abdomen of a patient after removal of the sheath.
Figure 1B:
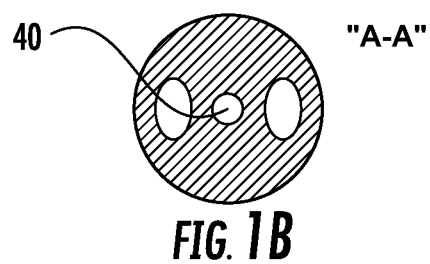
FIG. 1B is a cross-sectional view of the present inventive catheter at the lines A-A of FIG. 1A showing an upstream single inflow tube and a single outflow tube, prior to the splitting of each into a plurality of inflow and outflow auxiliary tubes, respectively, as well as a tube for selective receipt of a fiber optic scope.
Figure 1C:
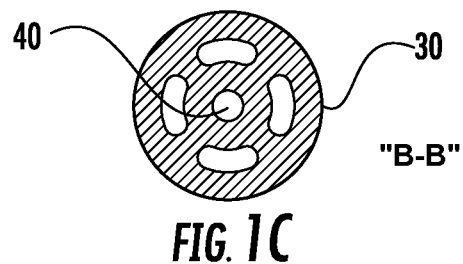
FIG. 1C is a cross-sectional view of the present inventive catheter at the lines B-B of FIG. 1A showing a plurality of smaller inflow tubes and a plurality of smaller outflow tubes after having been split from the single large inflow tube and single large outflow tube, and a tube for receipt of a fiber optic scope, all tubes being encased in an external covering.

FIG. 1A shows the preferred embodiment of present invention, a high open flux basket catheter for efficient continuous flow peritoneal dialysis (herein "basket catheter") as it would appear when fully-implanted and the sheath removed. Peritoneal dialysis is a form of dialysis necessitating a tube being inserted into a patient's abdominal cavity to introduce cleansing dialysis solution liquid, called dialysate, to the body. The walls of the abdominal cavity are lined with a membrane, called the parietal peritoneum, and the gut and other viscera are lined with peritoneal membrane called visceral peritoneum. The parietal and visceral peritoneums are continuous and thus form a cavity called peritoneal cavity. The peritoneal membrane along with peritoneal capillaries and other cells act as a "dialyzer" which allows waste products (uremic solutes and potassium) and excess body water to transport from the blood stream into the dialysis solution by the process of simultaneous diffusion and ultrafiltration. The dialysis solution is then drained from the abdomen, and takes with it the waste products which were previously cleared. The process of introducing the dialysis solution into the body and removing the unwanted fluids is called an exchange, and the period of time in which the dialysis solution is in the abdomen is called the dwell.

The open basket catheter 11, for use in peritoneal dialysis, is designed to maximize the efficiency of the dialysis procedure while minimizing the dwell time required for such. The open basket catheter 11 includes an inflow tunnel or tube 1, which carries dialysis solution into the peritoneal cavity, and an outflow tunnel or tube 2, which removes unwanted fluids and waste from the cavity of the body.

Within the principal catheter lumen, the main inflow tube 1 and the main outflow tube 2 are designed to split into a plurality of smaller tubes with tubular lengths. Inflow tube 1 and outflow tube 2 are adapted to connect at base 20. At base 20, shown as cross-sectional indication "A-A" in FIG. 1A and seen in FIG. 1B, a single large-diameter external protective tube 30 extends toward the end of the catheter which gets inserted into the abdomen. External tube 30 extends from base 20 to end E where the auxiliary inflow and outflow smaller diameter tubes emanate and expand in basket-like formation. In the preferred embodiment of the present invention, the inflow tunnels bifurcates into two smaller-diameter auxiliary tubes or tubes 3 and 4, while the outflow tunnels or tube 2 preferably trifurcates into smaller-diameter auxiliary tunnels or tubes 5, 6, and 7. The split from a single inflow tube and a single outflow tube to auxiliary tunnels 3, 4, 5, 6, and 7 occurs preferably at base 20, and all auxiliary tunnels 3, 4, 5, 6, and 7 are encased in external tube 30 for ease of insertion into the abdomen. The smaller-diameter inflow auxiliary tubes or tubes 3 and 4 are lined with apertures 13 to enable the dialysate to flow out and reach the peritoneal membrane and for dialysis to take place. Likewise, the outflow auxiliary tubes or tubes 5, 6 and 7 contain similar spaced apertures (along the length and around the tubes) 13 which allow the unwanted waste and fluids to be collected in the outflow tube so as to exit the body.

All of the auxiliary tubes 3, 4, 5, 6 and 7 are connected to a distal end cap 8 on their distal ends, which seals and holds all of the tips of the auxiliary tubes together. The auxiliary tubes are also preferably held together with one or more Dacron cuffs, which are wrappings of synthetic fabric which surrounds the catheter and anchors it within the body tissues of the abdominal wall, so as to prevent accidental displacement. One Dacron cuff, outer cuff 10, is preferably placed on the tubing at the skin level, while the other Dacron cuff, inner cuff 9, is preferably placed around the catheter at the peritoneal location. Middle and terminal portions of the tubes are enclosed in a meshed length of sheath 12 (see FIG. 2), which is preferably substantially about 22 cm long. After implantation of the catheter 11, the sheath 12 is manually retracted backwards. This serves to release all smaller-diameter auxiliary tubes 3, 4, 5, 6 and 7 (as is shown in FIG. 1). When the auxiliary tubes release, they open into an open basket shaped arrangement. Externally, tubes 3 and 4 of the catheter 11 provide the inflow tube 1 through intake 14, while tubes 5, 6 and 7 provide outflow tubes to the outflow tube 2 and to site 15, respectively, for the peritoneal dialysis apparatus.

Additionally, where inflow tube 1 and outflow tube 2 connect at base 20 to split into a plurality of auxiliary or separate tubes, there is preferably provided an additional tube 40 which runs parallel and through, extending the length of external tube 30, for receipt of a fiber optic borescope. This allows a physician conducting dialysis and using the present invention to see the inside of the peritoneal cavity to ensure proper functioning during the dialysis procedure. The tunnel 40 begins at the Y-shaped connection of inflow tube 1 and outflow tube 2 and external tube 30 at base 20. A cross-sectional view of the single inflow tube and single outflow tube where they meet at base 20 can be seen at cross-sectional view "A-A" in FIGS. 1A and 1B. A cross-sectional view of the plurality of auxiliary inflow and outflow tubes and the tube for selective receipt of the fiber optic scope can be seen at cross-section "B-B" in FIG. 1A and in FIG. 1C.

Once the auxiliary tubes are released from within the sheath, the catheter 11 within the peritoneal cavity allows the dialysis exchange to occur. The dialysate enters the body through inflow tube 1, and through apertures 13. Since multiple auxiliary inflow tubes 3 and 4 are present, the dialysate can reach all areas of the peritoneal cavity continuously. The preferred embodiment of the present invention utilizes two inflow auxiliary tubes. However, it is envisioned that any plurality of inflow tubes could be used in the present invention. The present invention allows dialysate to continuously flow from the dialysis machine, through inflow tube 1 and inflow auxiliary tubes 3 and 4 and into the peritoneal cavity.

Due to the basket shape of the catheter system, the present invention also allows for the increased effective peritoneal surface area to act as dialysis membrane. Larger surface area and uninterrupted exchange of fluids between the blood in peritoneal capillaries and dialysate augments clearance of unwanted waste and fluids to continuously exit the body. Like with the inflow auxiliary tubes, multiple outflow auxiliary tubes are utilized, which spread throughout the peritoneal cavity. Again, due to basket shape of the catheter in the peritoneal cavity, bowel loops and omentum do not block the effluent through the out flow tubes and thus peritoneal fluid removal is maximized. This allows for the unwanted waste to be cleared from the blood compartment faster, which significantly reduces the dwell period under which a patient would previously have had to wait while the exchange took place. While the preferred embodiment of the present invention utilizes three outflow auxiliary tubes, it is envisioned that any plurality of outflow tubes could be used in the present invention.

FIG. 2 depicts a present inventive catheter device 11. The middle and terminal portions of the catheter are covered by a sheath 12. Sheath 12 also holds together and in place portions of the inflow auxiliary tubes 3 and 4 and the outflow auxiliary tubes 5, 6 and 7. All tubes are connected at their distal ends by end cap 8 and by the proximal end within external tube 30. Upon implantation into the peritoneal cavity, sheath 12 will be retracted backwards and out of the abdomen, thereby deploying and separating inflow auxiliary tubes 3 and 4 and outflow auxiliary tubes 5, 6 and 7. The inflow and outflow auxiliary tubes preferably deploy in a basket-like manner, as is depicted in FIG. 3.

Figure 4:
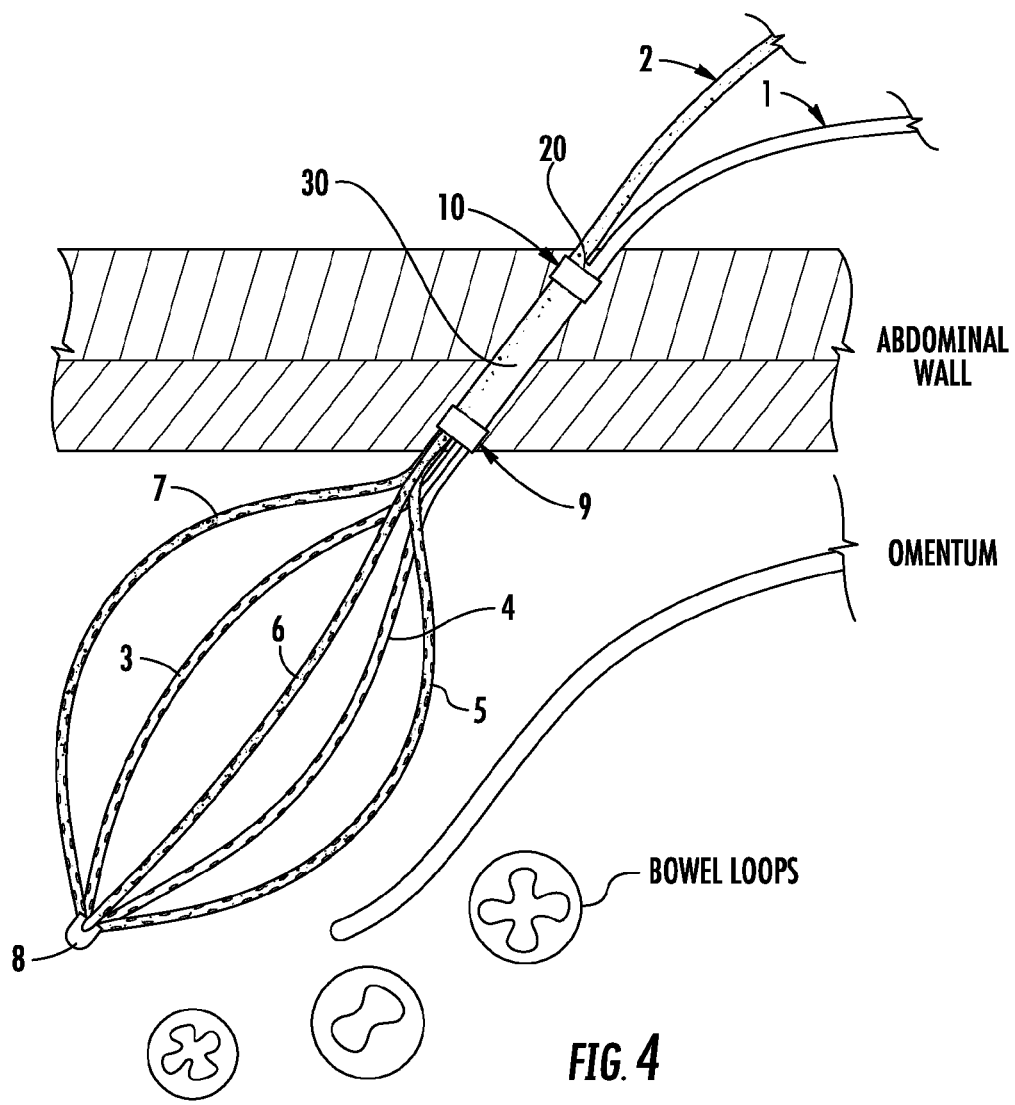
FIG. 4 is a side cross-sectional and perspective view of the device of FIG. 1, shown after placement into the peritoneal cavity.

FIG. 4 provides a schematic cross-sectional view of the novel, peritoneal-dialysis catheter 11, as would be seen when implanted into the peritoneal cavity. The design of the present invention acts to prevent blockages of the apertures 13 in the auxiliary tubes. In all previously known peritoneal dialysis catheters, there is no structure which prevents bodily organs, such as bowel loops, from lodging in next to the catheter and blocking the inflow or outflow of fluid. The present invention overcomes that obstacle in a manner seen in FIG. 4. The inflow and outflow tubes form a longitudinally separated basket-like shape. As can be seen, one external Dacron cuff (holding the tubes together) is preferably located inside the abdominal wall, within the subcutaneous tissue, while another internal Dacron cuff is preferably located within both the abdominal wall and the peritoneal membrane.

Figure 5:
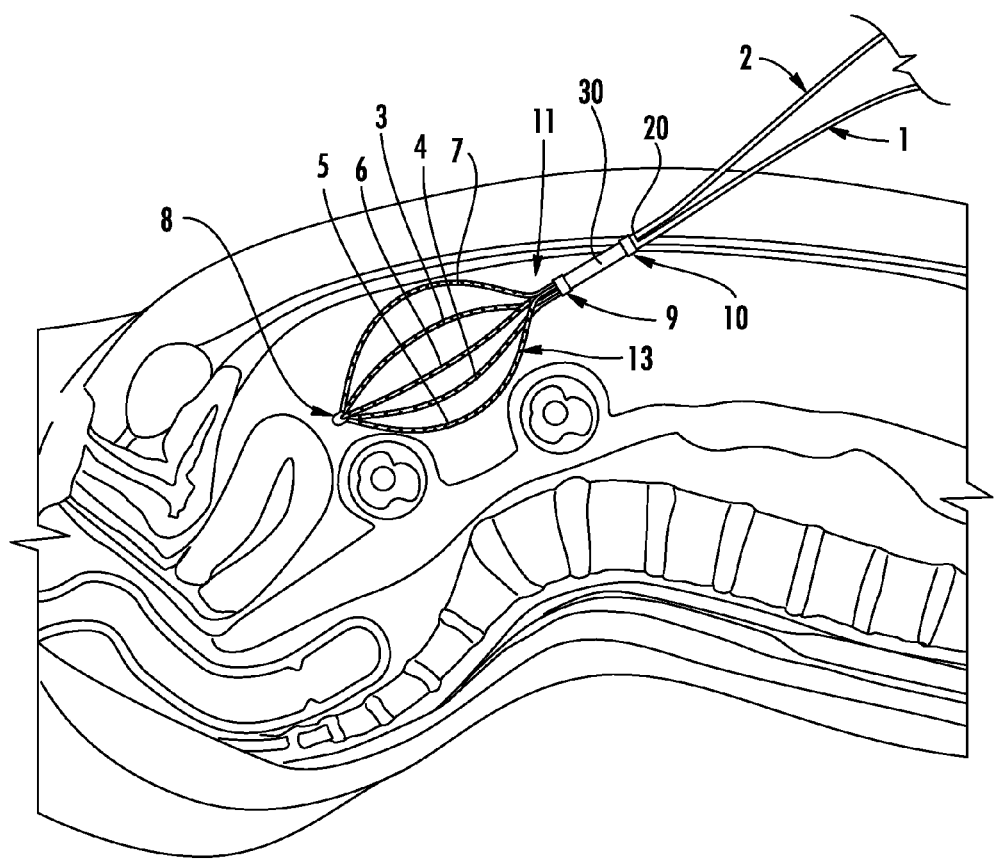
FIG. 5 is a cross-sectional view of the present invention as would be seen inside the peritoneal cavity.

FIG. 5 is a cross-sectional view of the present invention as would be seen implanted within the peritoneal cavity, a view showing a patient is lying in the supine position. The catheter 11 of the present invention, once fully-deployed within the body, will expand and separate into the peritoneal cavity and open up into a basket-like shape, expanding into small pockets so as to maximize the peritoneal surface area for exchange. As can be seen, the inflow and outflow auxiliary tubes cover a broad area within the peritoneal cavity to continuously bring dialysate to larger areas of the peritoneal membrane, thereby maximizing the concentration gradient across the membrane (through more frequent and continuous exchanges) while simultaneously maximizing removal of peritoneal fluids and solute waste. The present invention not only provides a broad surface area within the cavity, but it uses its own shape, when deployed, to prevent the bowel loops and other internal organs from blocking the apertures 13 in the auxiliary tubes 3, 4, 5, 6 and 7. Similarly, the shape of the present invention does now allow the catheter 11 to migrate from the implanted position and block the flow of dialysate, because all auxiliary tubes are held together by a preferably round, non-traumatic end cap 8.

Figure 6A:
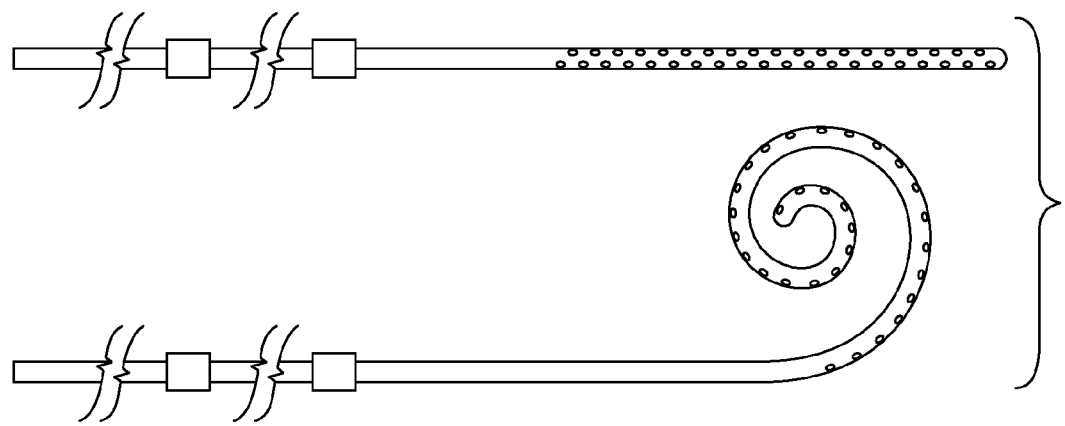
FIG. 6A depicts a prior art catheter used currently in peritoneal dialysis.
Figure 6B:
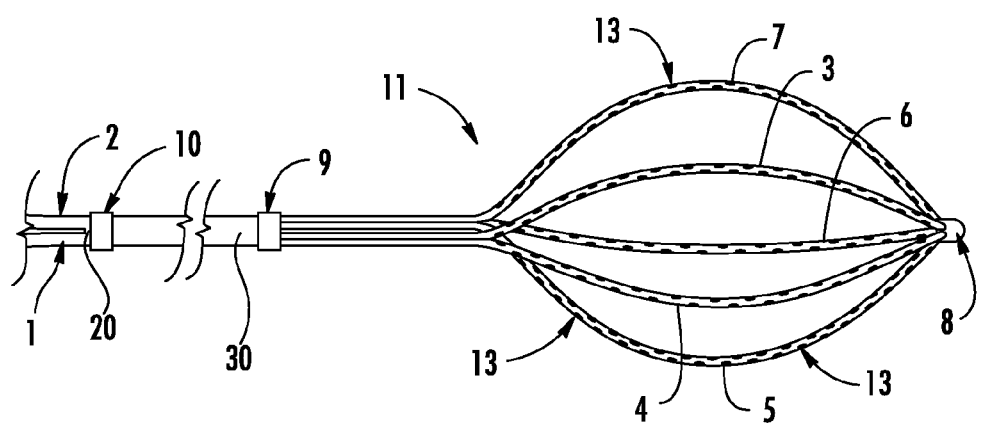
FIG. 6B is a side perspective view of the device shown in FIG. 1.

FIG. 6A depicts a common prior art catheter used in peritoneal dialysis. As can be seen, the catheter includes only one tube, which acts to control both the inflow and outflow of dialysate. Thus, in the prior art, dialysate must enter the body, sit for a period of time (called the dwell) to allow the solution to exchange with the unwanted waste in the body, and then be slowly drained, all through the same single tube. This not only takes a great deal of time, but is inefficient, as solution can only exit the catheter in one location in the peritoneal cavity. While the commonly used coiled (Tenckhoff) catheters prevent some omental wrap around the catheter, it does not increase the effective surface area of the peritoneal membrane to participate in dialysis exchange. Also in prior art using a single tube for both inflow and outflow of the dialysate, recirculation of dialysate can not prevented and thus efficiency of dialysis and clearance of solute or the waste products is reduced. FIG. 6B, comparatively, shows the present invention, a high-flux open basket catheter for peritoneal dialysis, which includes several inflow and outflow tubes, each of which serve a single function, not a dual function as the prior art—both inflow and outflow, thus providing continuous inflow and outflow of the dialysis solution, which can be achieved only with double lumen, not with prior art catheters.

Compared to prior art catheters, the present invention allows maximal exposure of the peritoneal membrane to the fluid during a single passage of the dialysate without recirculation. Due to fresh and continuous supply of the dialysate available for the exchange, a maximum concentration gradient can be achieved for solute removal across the peritoneal membrane. In the present invention, because of continuous flow of dialysate, less dwell volume is required which can result in less or no abdominal discomfort for a patient, compared to larger dwell volumes needed in traditional CCPD, APD and NIPD. In prior art catheters, during the terminal part of the outflow phase, lesser dwell volumes allow the bowel loops and omentum to move closer to, and block, the catheter tip and side holes and interrupt the outflow of dialysate.

There is also no exchange or transport of the solute and water occurring during the out flow phase using the prior art catheter. The present invention uses separate inflow and out flow tubes to maximize time of exchange, the concentration gradient, the effective peritoneal surface area, the efficiency of peritoneal fluid removal.

Figure 7A:
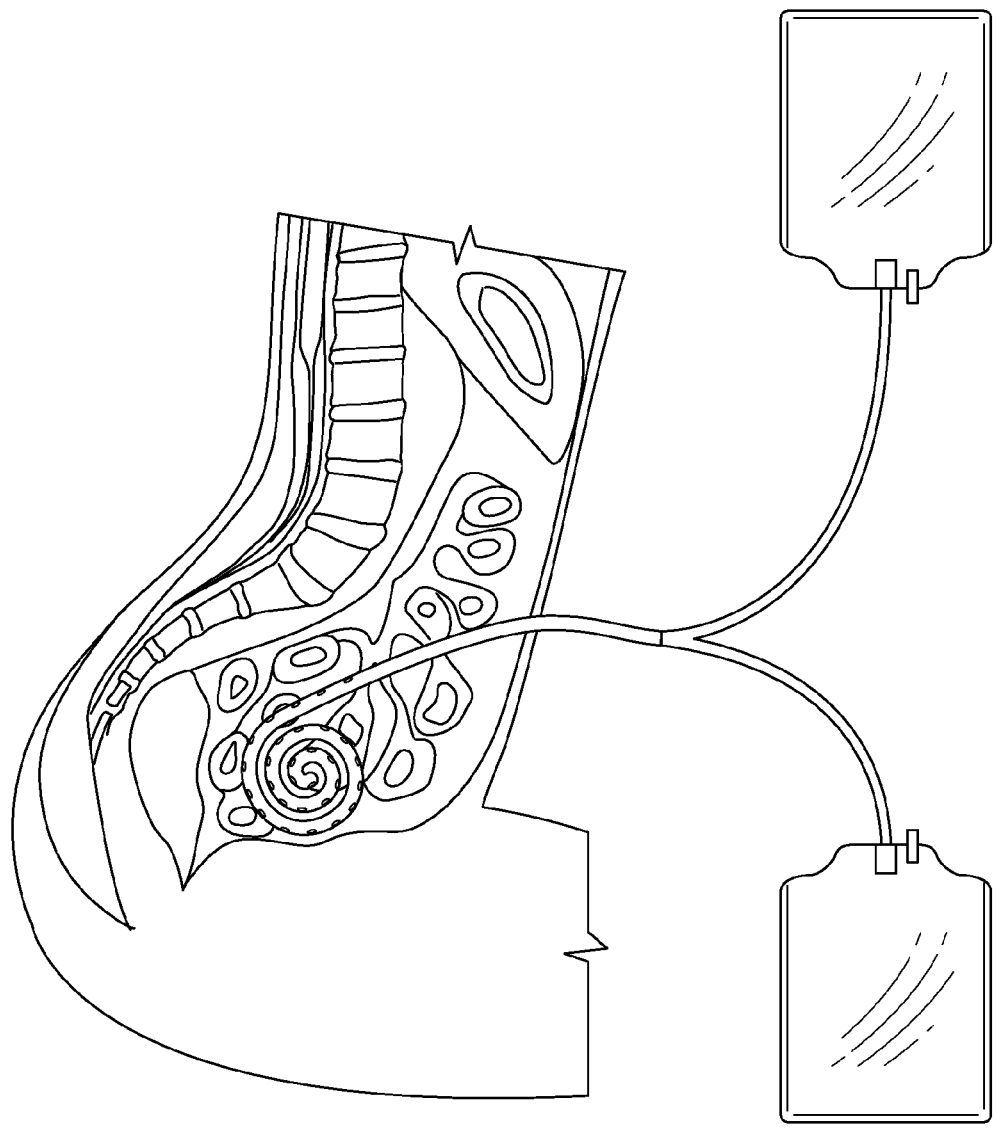
FIG. 7A depicts another prior art catheter as would be seen in use in the peritoneal cavity.

FIG. 7A shows a standard prior art catheter in the implanted position discussed in FIG. 6A. During the drainage of the solution and unwanted waste, resistance to fluid outflow increases as the omentum and bowel loops are brought close to the catheter and thereby block the side perforations. This, in turn, often causes outflow failure or at least diminished capacity. Also shown in FIG. 7A is the catheter kinking on itself while compressed in between the bowel loops.

Figure 7B:
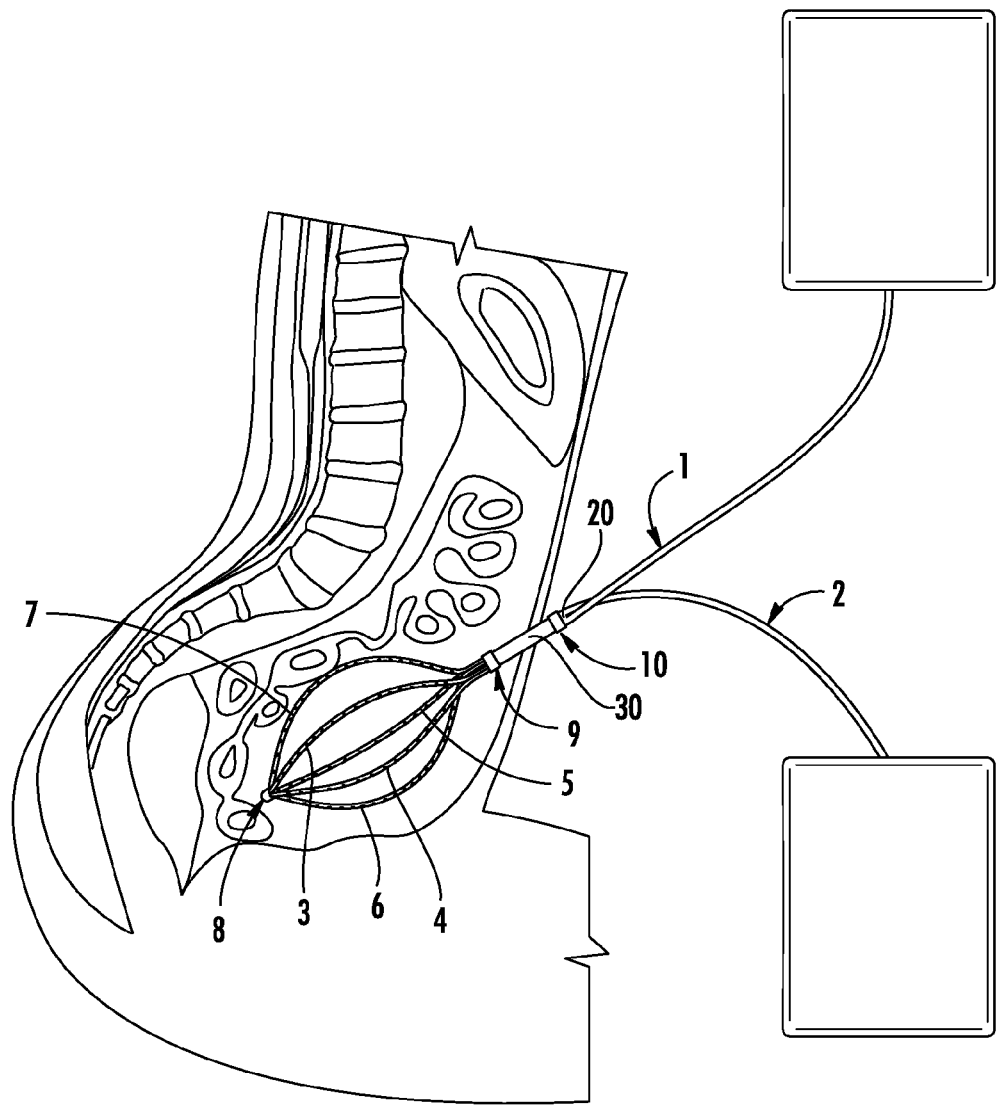
FIG. 7B is a side perspective and cross-sectional view of the present invention as would be seen inside the peritoneal cavity of a patient user.

Shown in FIG. 7B, the present invention overcomes both types of blockages common in the prior art, whether by bowel loops and omentum or by the catheter itself. Shown is the present invention catheter 11 after implantation, where the bowel loops are pushed aside by the catheter's own open-basket, separated structure. Therefore, the present invention improves dialysate inflow distribution, increases contact of the peritoneal membrane, and minimizes, or eliminates, outflow failure. This intra-abdominal portion of the catheter also facilitates continuous, simultaneous inflow and outflow through the catheter tubes, thereby drastically reducing the time required for the exchange to occur within the system. Dialysate is constantly flowing into the peritoneal cavity, clearing with the excess of water and solute, which transports through the membrane and exits the system in one continuous motion of fluids.

It will be understood by those of ordinary skill in the art that various changes may be made and equivalents may be substituted for elements without departing from the scope of the invention. In addition, many modifications may be made to adapt a particular feature or material to the teachings of the invention without departing from the scope thereof. Therefore, it is intended that the invention not be limited to the particular embodiments disclosed, but that the invention will include all embodiments falling within the scope of the claims.

What is claimed is:

1. A catheter for use in continuous flow peritoneal dialysis, comprising:
    an inflow tube, comprising a length of tubing having an inner diameter and an outer diameter, said inflow tube divided into a plurality of separate inflow auxiliary tubes, said inflow auxiliary tubes configured to pass dialysis fluid directly from said inflow tube to a peritoneal cavity; and
    an outflow tube, comprising a length of tubing having an inner diameter and an outer diameter, said outflow tube divided into a plurality of separate outflow auxiliary tubes, said outflow auxiliary tubes configured to pass dialysis fluid directly from the peritoneal cavity to said outflow tube;
    wherein each of said inflow tube and said outflow tube has a proximal connection means for securing to a dialysis machine;
    wherein each of said inflow auxiliary tubes and said outflow auxiliary tubes contains a plurality of fluid-conveying apertures for simultaneous movement of dialysis fluid in and out of the peritoneal cavity;
    wherein at least a segment of said inflow auxiliary tubes and said outflow auxiliary tubes are encased in a single, outer tube, said outer tube further comprising a separate tube which is adapted for receipt of a fiber optic borescope for viewing the dialysis procedure;
    wherein said inflow auxiliary tubes and said outflow auxiliary tubes define an expandable open-basket shape, and wherein all of said auxiliary tubes are separate and connected at their distal ends by a non-traumatic end cap; and
    wherein said apertures on said inflow auxiliary tubes and said apertures on said outflow auxiliary tubes throughout the perimeter of said open-basket shape are configured to provide unobstructed free-flow of dialysis fluid throughout the peritoneal cavity while maximizing the surface area of the peritoneal cavity directly targeted by the dialysis fluid released from said apertures in said inflow auxiliary tubes.

2. The catheter for use in continuous flow peritoneal dialysis as claimed in claim 1, wherein the number of inflow auxiliary tubes is preferably two.

3. The catheter for use in continuous flow peritoneal dialysis as claimed in claim 1, wherein the number of outflow auxiliary tubes is preferably three.

4. The catheter for use in continuous flow peritoneal dialysis as claimed in claim 1, wherein the number of said outflow auxiliary tubes is greater than the number of said inflow auxiliary tubes.

5. The catheter for use in continuous flow peritoneal dialysis as claimed in claim 1, wherein a retractable sheath is initially provided over said inflow and outflow auxiliary tubes prior to expansion of the open-basket configuration.

6. The catheter for use in continuous flow peritoneal dialysis as claimed in claim 1, wherein each of said inflow tube and said outflow tube has an inner diameter of about 2.5 mm.

7. The catheter for use in continuous flow peritoneal dialysis as claimed in claim 1, wherein each of said inflow tube and said outflow tube preferably has an outer diameter of about 4.0 mm.

8. The catheter for use in continuous flow peritoneal dialysis as claimed in claim 1, wherein said apertures on said inflow auxiliary tubes and said outflow auxiliary tubes are preferably no larger than 0.5 mm.

9. The catheter for use in continuous flow peritoneal dialysis as claimed in claim 1, wherein said end cap is preferably round.

10. The catheter for use in continuous flow peritoneal dialysis as claimed in claim 1, wherein said single, outer tube is preferably about 320 mm long.

11. The catheter for use in continuous flow peritoneal dialysis as claimed in claim 1, wherein said single, outer tube preferably has an inner diameter of about 3.5 mm.

12. The catheter for use in continuous flow peritoneal dialysis as claimed in claim 1, wherein said single, outer tube preferably has an outer diameter of about 4.0 mm.

13. The catheter for use in continuous flow peritoneal dialysis as claimed in claim 1, wherein said single, outer tube connecting to said inflow tube and said outflow tube at a base section, said base section defining a Y-shaped connection at said inflow tube and said outflow tube.

14. The catheter for use in continuous flow peritoneal dialysis as claimed in claim 1, wherein said two or more smaller inflow auxiliary tubes and said two or more smaller outflow auxiliary tubes extend within and through said outer tube.

\* \* \* \* \*